(12) United States Patent
Rosenberg et al.

(10) Patent No.: US 9,314,650 B2
(45) Date of Patent: *Apr. 19, 2016

(54) METHOD AND APPARATUS FOR TREATMENT OF ADIPOSE TISSUE

(75) Inventors: Avner Rosenberg, Beit Shearim (IL); Shimon Eckhouse, Haifa (IL); Michael Kreindel, Zichron Ya'acov (IL)

(73) Assignee: SYNERON MEDICAL LTD., Yokneam Illit (IL)

( * ) Notice: Subject to any disclaimer, the term of this patent is extended or adjusted under 35 U.S.C. 154(b) by 247 days.

This patent is subject to a terminal disclaimer.

(21) Appl. No.: 13/369,583

(22) Filed: Feb. 9, 2012

(65) Prior Publication Data

US 2012/0136280 A1 May 31, 2012

Related U.S. Application Data

(63) Continuation of application No. 11/355,181, filed on Feb. 16, 2006, now Pat. No. 8,133,191.

(51) Int. Cl.
*A61N 7/00* (2006.01)
*A61N 1/04* (2006.01)
*A61N 1/32* (2006.01)
*A61B 17/00* (2006.01)
*A61B 19/00* (2006.01)
*A61B 18/12* (2006.01)
*A61B 18/00* (2006.01)

(52) U.S. Cl.
CPC ............. *A61N 7/00* (2013.01); *A61N 1/0408* (2013.01); *A61N 1/0472* (2013.01); *A61N 1/328* (2013.01); *A61B 18/12* (2013.01); *A61B 2017/00026* (2013.01); *A61B 2017/00061* (2013.01); *A61B 2017/00106* (2013.01); *A61B 2018/0047* (2013.01); *A61B 2019/5276* (2013.01); *A61N 2007/0008* (2013.01); *A61N 2007/0039* (2013.01); *A61N 2007/0078* (2013.01)

(58) Field of Classification Search
CPC ... A61N 1/0408; A61N 1/0472; A61N 1/328; A61N 7/00; A61N 2007/0008; A61N 2007/0039; A61N 2007/0078; A61B 18/12; A61B 2017/00026; A61B 2017/00061; A61B 2017/00106; A61B 2018/0047; A61B 2019/5276
See application file for complete search history.

(56) References Cited

U.S. PATENT DOCUMENTS

| | | | |
|---|---|---|---|
| 5,350,964 A * | 9/1994 | Hara et al. | 310/357 |
| 6,500,141 B1 * | 12/2002 | Irion et al. | 604/22 |
| 7,530,958 B2 * | 5/2009 | Slayton et al. | 601/2 |
| 2004/0206365 A1 * | 10/2004 | Knowlton | 128/898 |
| 2004/0267252 A1 * | 12/2004 | Washington et al. | 606/27 |

(Continued)

*Primary Examiner* — Bo J Peng
(74) *Attorney, Agent, or Firm* — Vorys, Sater, Seymour and Pease LLP; William L. Klima

(57) ABSTRACT

The invention provides methods and apparatuses for the treatment of adipose tissue. The methods comprise application of ultrasound energy to a region of adipose tissue, and the apparatuses comprise at least one source of ultrasound energy configured to direct ultrasound energy through a skin surface into the subcutaneous adipose tissue. In one embodiment, a pressure gradient is created in the region generating relative movement between fat cell constituents having different densities. In another embodiment, a protrusion of skin and underlying adipose tissue containing is formed and ultrasound energy is radiated into the adipose tissue in the protrusion. In another embodiment, an RF electric field is generated inside a region of adipose tissue together with the ultrasound energy.

18 Claims, 13 Drawing Sheets

(56) References Cited

U.S. PATENT DOCUMENTS

2006/0047215 A1* 3/2006 Newman et al. ............. 600/513
2006/0074313 A1* 4/2006 Slayton et al. ............... 600/439
2006/0089637 A1* 4/2006 Werneth et al. ............... 606/41

* cited by examiner

METHOD AND APPARATUS FOR TREATMENT OF ADIPOSE TISSUE

This is a Continuation Application filed under 35 U.S.C. §120 as a continuation of U.S. patent application Ser. No. 11/355,181, filed on Feb. 16, 2006, the content of which is hereby incorporated by reference in its entirety.

FIELD OF THE INVENTION

The invention relates to methods and apparatuses for the reduction of adipose (fat) tissue.

LIST OF REFERENCES

The following references are brought to facilitate description of the background of the present invention, and should not be construed as limiting the scope or patentabililty of the invention:
U.S. Pat. No. 5,143,063
U.S. Pat. No. 5,158,070
US Patent Applications Nos. 2005/0154431 and 2004/0106867
U.S. Pat. No. 6,607,498
U.S. Pat. No. 6,113,558
U.S. Pat. No. 6,889,090
U.S. Pat. No. 5,871,524
U.S. Pat. No. 6,662,054
S. Gabriel, R. W. Lau, and C. Gabriel, Phys. Med. Biol. 41 (1996),pp 2251-2269
Luc Fournier and Be'la Joo's, Physical review 67, 051908 (2003)
Alster T. S. and Tanzi, E. L., The Journal of Cosmetic and Laser Therapy. 2005; 7: 81-85
"Physical properties of tissue", by Francis A. Duck, Academic Press Ltd., 1990, p. 138, the density of adipose tissue is 916 Kg/m$^3$
"Physical properties of tissue", by Francis A. Duck, Academic Press Ltd., 1990, p. 85 Herve Isambert, Phys. Rev. Lett. 80, p 3404 (1998)
K. Y. Saleh and N. B. Smith, Int. J. Hyperthermia Vol. 20, NO. 1 (February 2004), pp. 7-31.

BACKGROUND OF THE INVENTION

Reduction of subcutaneous fat layers, or adipose tissue, is an aesthetic treatment for which there is a growing demand. One method, liposuction, is a very aggressive invasive treatment requiring local or general anesthesia, and the subsequent healing process is very long and painful. Methods for non-invasive local reduction of fat are based on the delivery of electromagnetic or sound energy through the skin into the subcutaneous adipose tissue. The main challenge with non-invasive treatment of fat tissue is to transfer the energy through the outer layers of the skin, and concentrating it to the required level in the fat tissue with minimal collateral damage to the skin layers and deeper body tissues.

U.S. Pat. No. 5,143,063 describes a method for destruction of fat cells (adipocytes) in subcutaneous adipose tissue, in which radiant energy is focused into these cells. The radiant energy may be electromagnetic in the microwave range, or ultrasound. The major mechanism for cell destruction is the heat generated by the radiant energy. Only at the focal volume is the energy density high enough for cell destruction, while outside the focal volume the energy density is lower than the damage threshold. There is no specific selectivity for destruction of fat cells, only a geometrical selectivity created by the focusing.

U.S. Pat. No. 5,158,070 discloses use of ultrasound pulses of short duration that are powerful enough to tear soft tissue. Ultrasound pulses having a frequency between 3 MHz to 10 MHz and a pulse length of one μsec to one msec are focused in the soft tissue to effect tearing and destruction. Due to the application of short intense pulses, mechanical, and not thermal, effects are presumed to be responsible for the tissue destruction. The following calculation provides an estimate for the peak pressure of the ultrasound wave required for this cell tearing. Assuming a plane ultrasound wave for which the cell size is much smaller then the wavelength, the local displacement U(x) is given by:

$$U(x)=U_{max}\sin(\omega t-kx)$$

where $U_{max}$ is the maximum displacement given by:

$$U_{max}=\frac{V_{max}}{\omega}$$

$V_{max}$ is the maximum velocity, $\omega=2\pi f$, f is the frequency of the ultrasound, and k is the wave vector. For a plane wave, $\omega=kc$, where c is the sound velocity at the tissue. Taking the derivative of U with respect to x, the strains obtained:

$$\frac{dU}{dx}=-k\frac{V_{max}}{\omega}\cos(\omega t-kx)=\frac{-V_{max}}{c}\cos(\omega t-kx)$$

The maximal strain is $V_{max}/c$. The strength of a typical cell membrane has been investigated, and it was found that stretching a cell membrane by more then 2% causes it to tear, leading to cell necrosis, (Luc Fournier and Be'la Joo's, Physical review 67, 051908 (2003)). This corresponds to a strain of 0.02. Since the sound velocity in a typical soft tissue is about 1500 m/sec, for rupturing a cell membrane, $V_{max}$ has to be over 30 m/sec. For a plane wave, V=P/Z, where P is the pressure and Z is the acoustic impedance of the tissue, a typical value for Z is 1.5 MRayleigh, so that P has to be greater than 45 MPa. This number corresponds to a very intense ultrasound, which can be achieved with a very high degree of focusing, and which is obtainable at frequencies in the range of a few MHz. For example, US Patent Application No. 2005/0154431, discloses adipose tissue destruction generated by HIFU (High Intensity Focused Ultrasound), with a typical frequency of 1-4 MHz and a pressure of about 30 MPa, close to the theoretical estimate of 45 Mpa obtained above.

This method of cell rupturing is also not selective for adipose tissue cells (adipocytes) because the adipocyte membrane is not weaker than that of other cells. Also the shape and size of the cell did not enter in the above considerations. In this respect, cell destruction by rupturing the cell membrane is similar to cell destruction by heating the cells (hyperthermia). Neither method is selective for adipocytes, and any selectivity in the method relies on geometry i.e. very strong focusing of the radiation in the adipose tissue. For both methods, a high degree of focusing yields a very small focal volume where cell destruction occurs. A typical effective focal width is a few millimeters. Therefore, the focal volume has to be moved over the treated area. US Patent Applications Nos. 2005/0154431 and 2004/0106867 disclose such a system.

Another physical effect of focused ultrasound that can cause cell lysis, is cavitations. Cavitations are small bubbles, starting from initial small gas nucleation centers, which are driven larger by the negative pressure phase of the ultrasound wave. The rate of generation and growth of cavitations is an increasing function of the amplitude of the pressure, therefore an increasing function of the ultrasound power density. Under certain critical conditions, the bubbles collapse violently, generating in their vicinity shock waves and fluid jets that can destroy cells. In liquid environments, especially in aqueous solutions, there is evidence that collapse of cavitations causes cell gnecrosis and apoptosis. U.S. Pat. No. 6,607,498 discloses focusing ultrasound energy on adipose tissue to cause cavitations and lysis of adipose tissue. U.S. Pat. No. 6,113,558 discloses the application of focused pulsed ultrasound, which causes cavitations, for non-invasive treatment of tissues. This last patent contains a list of possible applications, which include the induction of apoptosis and necrosis, clot lysis, and cancer treatment. This patent includes a study on the generation of cavitations and on the optimization of pulse width and pulse repetition rate for maximizing the cavitations. The cavitation threshold for a non-degassed buffer solution and blood are in the range of 1000-1500 W/cm$^2$, while for degassed fluids the threshold rises to 2000 W/cm$^2$. The ultrasound frequency in these experiments was 750 kHz. Cavitation damage is not cell selective, and can be induced on many cell types. The cavitation threshold is quite high, and can be expected to be much higher inside adipose tissue, since most of the tissue volume is fat (lipid vacuoles). As with thermal treatment and mechanical rupturing of cells by ultrasound, also with cavitation, a high degree of focusing is required to ensure treatment of the selected tissue only (geometrical selectivity). There is another reason for the importance of focusing in cavitation treatment: Cavitations absorb ultrasound very strongly. Therefore, if cavitations are created close to the applicator, that is between the focal region and the ultrasound radiating transducer (for example at the skin), then most of the ultrasound energy will be dissipated there and will not reach the target tissue in the focal volume. To prevent this from occurring, the focusing must be sufficient to assure an intensity above the minimum value for cavitation at the focal volume, while the intensity at other tissues between the transducer and focal volume must be below the threshold for cavitation.

Besides ultrasound and microwave radiation, application of RF (Radio Frequency) energy can affect both the skin and subcutaneous layers. U.S. Pat. No. 6,889,090 discloses the application of RF energy for skin treatment. U.S. Pat. No. 5,871,524, describes application of radiant energy through the skin to an underlying subcutaneous layer or deeper soft tissue layers. The main energy source is RF. A bi-polar RF application, such as described in U.S. Pat. No. 6,889,090, is preferred over unipolar RF, since in unipolar RF currents flow through uncontrolled channels at the body, and may cause unwanted damage.

RF energy is applied to the body through two conducting electrodes applied to the skin between which an alternating voltage is driven. The RF current flows according to Ohm's law through the conducting tissues, generating heat, which can affect the tissue. The conductivity of the skin layers is an order of magnitude larger than that of fat tissue. Typical skin conductivity is about 0.45/m and that of adipose tissue is about 0.045/m at RF frequencies between 100 kHz and 10 MHz (S. Gabriel, R. W. Lau, and C. Gabriel, Phys. Med. Biol. 41 (1996), pp 2251-2269). Therefore most of the current flows through the skin layers, which is good for skin treatments, for example, hair removal and skin rejuvenation. However, it is less efficient for treatment of the deeper adipose layers.

U.S. Pat. No. 6,662,054 discloses the application of negative pressure (vacuum) to a region of the skin, so that this region protrudes out of the surrounding skin, and applying RF energy to the protrusion via electrodes. Under negative pressure, the path between the RF electrodes is longer along the skin than through the subcutaneous layers. Therefore, more RF energy is delivered into subcutaneous layers than through the skin. A commercial system based on U.S. Pat. No. 6,662,054 has proved efficient for treatment of cellulites (TINA S. ALSTER & ELIZABETH L. TANZI, The Journal of Cosmetic and Laser Therapy. 2005; 7: 81-85). Cellulite is clinically manifested by irregular skin contours or dimpling of the skin. It is caused by excess adipose tissue retention within fibrous septae. The skin irregularity is proportional to the subcutaneous fat projected into the upper dermis.

Most of the volume of an adipocyte is occupied by a fat fluid drop, known as a lipid vacuole. The typical diameter of the cell is 50-100 µm It tends to 100 µm in adipose tissue of obese people. Between the lipid vacuole and cell membrane, is cytoplasm. Typically the width of the cytoplasm is only a few micrometers and it is not uniform around the lipid vacuole. It can be in the range from below 1 µm in one region of the cell and 3-5 µm in other regions.

The macroscopic physical properties of adipose tissue, mass density and sound velocity, are dominated by the material of the lipid vacuole, which occupies most of the tissue volume in mature fat cells which are the cells to be treated in reduction of the fat layer. The physical properties of the lipid vacuole fluid are thus almost identical to those of fat tissue. The density of adipose tissue is about 10% lower than that of other body tissues. According to "Physical properties of tissue", by Francis A. Duck, Academic Press Ltd., 1990, p. 138, the density of adipose tissue is 916 Kg/m$^3$, while that of body fluids and soft tissue are above 1000 Kg/m$^3$ (i.e. above the density of water). The dermis density is about 1100 Kg/m$^3$, while that of muscles is 1040 Kg/m$^3$. The cytoplasm and intercellular fluid are aqueous solutions so that their density is expected to be similar to that of other body fluids and soft tissues, i.e. in the range of 1020-1040 Kg/m$^3$. The velocity of sound is about 1430 m/sec in adipose tissue, compared to 1530 m/sec for skin, at normal body temperature. Moreover, on page 85 of the Duck reference, the slope of the sound velocity versus temperature curve for fat is completely different from that of other body fluids. For fat, sound velocity decreases with increasing temperature, dropping to 1400 m/sec at 40° C., while that of water and other body fluids rises with temperature, and is about 1520 m/sec at 40° C. for water and higher for body fluids and soft tissues other than fat.

A basic model of the electrical properties of cells at the microscopic level can be found in Herve Isambert, Phys. Rev. Lett. 80, p 3404 (1998). The cell membrane is a poor electrical conductor and therefore behaves essentially as a local capacitor upon the application of an electric field across the cell. The charging of the cell membrane under the application of external electric field generates a stress at these membranes, yielding strain which depends on the elastic properties of the cell, and which at increased intensity can rupture the cell membrane, a phenomena known as "electroporation".

SUMMARY OF THE INVENTION

The present invention provides methods and apparatuses for the treatment of adipose (fat) tissue. As used herein, the term "treatment of adipose tissue" includes such procedures as fat destruction, inducing fat necrosis, inducing fat apoptosis, fat redistribution, adipocyte (fat cell) size reduction, and cellulite treatment.

The apparatuses of the invention include at least one ultrasound transducer configured to be applied to a skin surface and to radiate ultrasound energy through the skin into the subcutaneous adipose tissue. The methods of the invention include directing adipose tissue through the skin layer into the subcutaneous adipose tissue.

One embodiment of the invention is based upon a new finding that pressure gradients of ultrasound energy can lead to selective treatment of the adipose tissue cells. Without wishing to be bound by a particular theory, it is believed that the treatment or destruction of adipose tissue cells by pressure gradients generated by ultrasound energy is due to differences between the mass density of the lipid and that of the other constituents of the adipocytes. As explained below, a pressure gradient in adipose tissue capable of treating or destroying the adipose tissue cells may be generated using a moderately focused ultrasound transducer.

In another embodiment of the invention, skin and a region of the underlying adipose tissue are made to protrude out from the surrounding skin surface. Ultrasound energy is then directed to adipose tissue in the protrusion. The protrusion may be formed, for example, by applying a negative pressure (vacuum) to the skin region or by mechanical manipulation of the skin region. The apparatus of this aspect of the invention includes an applicator adapted for causing a skin region to protrude above the surrounding skin region and one or more ultrasound transducers which radiate ultrasound energy preferably into the protrusion.

In yet another embodiment of the invention, ultrasound energy and RF energy are directed into the adipose tissue. The apparatus of this aspect of the invention includes an applicator having at least one pair of RF electrodes and at least one ultrasound transducer.

BRIEF DESCRIPTION OF THE DRAWINGS

In order to understand the invention and to see how it may be carried out in practice, preferred embodiments will now be described, by way of non-limiting examples only with reference to the accompanying drawings, in which.

DESCRIPTION OF THE INVENTION

Figure 1:
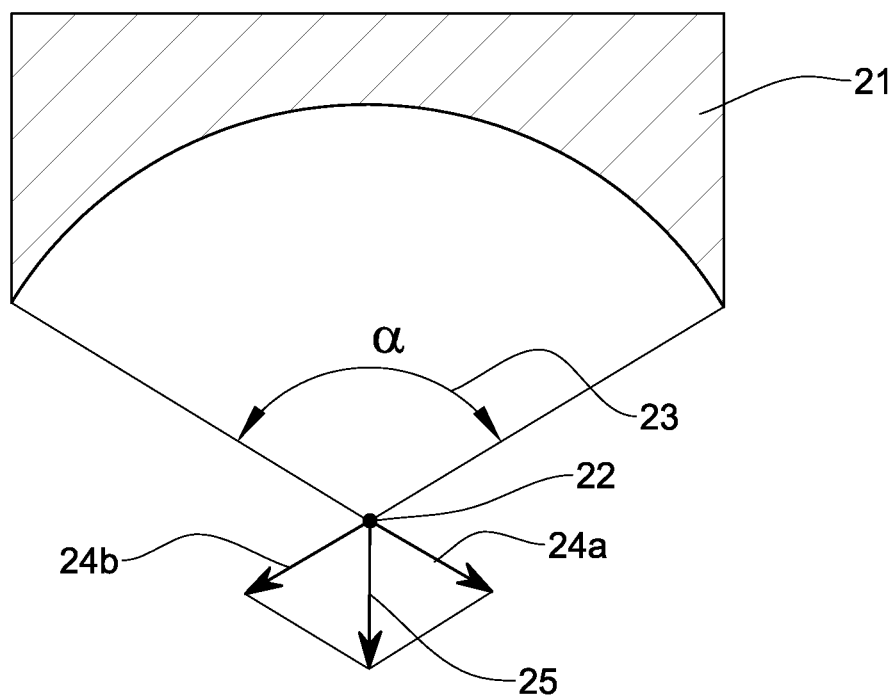
FIG. 1 shows the "view angle" of an ultrasound transducer and vector summation of pressure gradients.

The present invention provides methods and apparatus for treatment of adipocytes. One aspect of the invention is based upon a new finding that pressure gradients of ultrasound energy can lead to selective treatment of the adipose tissue cells. Without wishing to be bound by a particular theory, it is believed that the selective treatment of adipose tissue cells by pressure gradients generated by ultrasound energy is due to differences between the mass density of the lipid and that of the other constituents of the adipocytes.

When ultrasound energy is directed to a fat cell, for frequencies of less than about 1 MHz, the wavelength of the ultrasound wave is about 1.5 mm, much larger than the fat cell dimensions, which are 50-100 μm. For a plane acoustic wave propagating through the tissue having pressure amplitude $P_{max}$, angular frequency ω and wave vector k=2π/λ, where λ is the wavelength, the pressure p(x,t) is:

$$p(x,t) = P_{max} \sin(\omega t - kx) \quad (1)$$

Neglecting viscosity, the movement of fluids can be calculated from Euler's equation:

$$\frac{\partial \vec{v}}{\partial t} + (\vec{v} \cdot \nabla)\vec{v} = -\frac{1}{\rho} \nabla p \quad (2)$$

Where v is the velocity vector, and ρ is the mass density of the fluid. For small velocities (compared to the sound velocity c) the term (v∇)v can be neglected and the velocity is proportional to the pressure gradient. For the plane wave of equation 1, since the motion is only in the x-direction:

$$\frac{\partial v}{\partial t} = -\frac{1}{\rho} \frac{\partial p}{\partial x} = \frac{P_{max} k}{\rho} \cos(\omega t - kx) \quad (3)$$

The velocity is:

$$v(x, t) = \frac{P_{max} k}{\rho \omega} \sin(\omega t - kx) \quad (4)$$

And the local displacement of the fluid is:

$$U(x, t) = -\frac{k P_{max}}{\rho \omega^2} \cos(\omega t - kx) \quad (5)$$

This is the formula for a plane acoustical wave, and for such a wave ω=kc and $kP_{max}$ is the pressure gradient.

Let $\rho_{li}$ be the density of the fluid of the lipid vacuole, and $\rho_{cy}$ the density of the cytoplasm fluid in an adipocyte. The respective amplitudes of the displacements can be calculated using equation (5) and substituting the corresponding densities:

$$U_{li} = \frac{kP_{max}}{\rho_{li}\omega^2} \quad (6)$$

$$U_{cy} = \frac{kP_{max}}{\rho_{cy}\omega^2}($$

And the relative movement of the two fluids is given by:

$$\Delta U = U_{li} - U_{cy} = \frac{kP_{max}}{\omega^2}\left(\frac{1}{\rho_{li}} - \frac{1}{\rho_{cy}}\right) \quad (7)$$

Numerical Example

Taking typical values for the adipocytes, $\rho_{li}$=916 Kg/m³, $\rho_{cy}$=1020 Kg/m³, and taking $P_{max}$=4 MPa, $\omega$=2$\pi$f, f=250 kHz, and c=1400 m/sec, k=$\omega$/c=1122 m¹, the result is $\Delta U$=0.2 μm. The physical meaning is that the cytoplasm fluid, which is a "minority" fluid in the adipose tissue, oscillates under these conditions with respect to the "majority" fluid, the lipid vacuole, with an amplitude of 0.2 μm. The pressure of $P_{max}$=4 MPa corresponds to the power flow density of $P^2/2Z$=6.2 MW/m²=620 W/cm² and to a peak pressure gradient of $kP_{max}$=4.5 GPa/m A relative displacement of 0.2 μm is significant at the scale of cellular dimensions. The cytoplasmic layer in the adipocytes has a thickness of few micrometers, at some regions of the cell even below 1 μm. More specifically, there are regions of the cell where over a length of 5-10 μm the width of the cytoplasm changes from below one micrometer to few micrometers. At the narrower regions, the fluid movement of the cytoplasm is damped by viscosity, while at the wider regions the cytoplasm is freer to move. Under the conditions of this example, there is a difference of displacement of about 0.2 μm over a length of 5-10 μm, which means a strain of 0.04-0.02. Since the cell membrane borders the cytoplasm, the cell membrane is also subjected to that strain, which is above the threshold for membrane rupture.

Another effect that may be associated with the above relative movement of adipocyte fluids is selective heating of the cytoplasm. The viscosity will cause some of the kinetic energy to be converted into heat. Since the cytoplasm is a minority fluid in the fat tissue and since the lipid vacuole fluid has poor heat conductance, the generated heat will selectively raise the temperature of the cytoplasm and of the cell membrane bordering it, and may lead to cell necrosis or apoptosis, directly by the local temperature rise at the membrane, or by lowering its strength at the elevated temperature.

For a non-plane wave, $kP_{max}$ in equation 7 must be replaced by the more general pressure gradient, $\nabla P$, in accordance with Euler's equation. It is known to use focusing of the ultrasound energy to generate very high power densities in a focal volume. It helps in two ways: first, it facilitates production of high power densities by an ultrasound transducer, and, second, it generates geometrical selectivity for the desired effect at the focal volume. However it should be noted that focusing, especially strong focusing, enhances the peak pressure substantially more than the pressure gradient. As a limiting example, a spherical transducer will generate at its center a very high peak pressure but zero pressure gradient, a manifestation of the fact that at the center the fluid is not moving. The focusing may be described physically as a superposition of plane waves. The pressure amplitude is a scalar, and at the focus the phases of the plane waves are identical, therefore the pressure at the focus is a scalar sum of the pressure amplitudes. However, the pressure gradient, and the displacement which is proportional to that gradient (by Euler's equation), are vectors, therefore their vector summed amplitude is always smaller than the sum of the magnitudes. More specifically, for strong focusing, the ultrasound radiation arrives at the focus from directions with large angular deviations, reducing the vector sum of the pressure gradient and of the fluid displacement. Therefore, according to the invention, it is preferred to limit the focusing in order to enhance the pressure gradient at the expense of the pressure amplitude at the focus, so that the selective effects on the fat cell will be obtained with undesired effects associated with high pressure, such as cavitations.

According to invention, based on the above considerations, an apparatus for selective destruction of fat cells will include an ultrasound transducer, which is moderately focused. Referring to FIG. 1, an ultrasound transducer 21 has a focal point 22. The view angle $\alpha$ of the transducer edges from the focal point correlates with the focusing in a very general way: The larger a the larger the focusing. The displacement and the pressure gradient at the focus generated by waves coming from the edges of the transducer, is the vector sum of vector 24a and vector 24b yielding vector 25. The magnitude of the vector 25 is the magnitude of the vector 24a multiplied by 2 cos($\alpha$/2) (assuming 24a is equal to 24b). For $\alpha$=120° this factor is 1, compared to a factor of 2 for the scalar summation of the pressure at the same point. That is, for large $\alpha$ the pressure is enhanced by the focusing much more then the pressure gradient. Therefore, to obtain the selective fat reduction according to the invention, the angle $\alpha$ is limited. Preferred values are $\alpha$<120°, more preferred $\alpha$<90°.

According to the invention, based on equation 7, for selective destruction of fat cells it is preferred to radiate the ultrasound at low frequencies, preferably lower than 1 MHz, more preferred below 300 kHz. The numerical example above demonstrated that at 250 kHz peak pressure gradient of 4.5 GPa/m is expected to selectively damage fat cells. For moderate focusing this corresponds to a power flow density of about 700 W/cm², which is lower than the threshold for cavitation, which is preferably avoided according to the invention.

Pulsed operation is another way according to the invention for enhancing the selective effects of the ultrasound for cell destruction. Short pulses with high intensity generate high strain at the cell membranes due to the high pressure gradients, while the average power is low enough to prevent non-selective damage by excessive heating of tissues. Also, for selectively heating of cytoplasm and cell membranes by viscosity it is preferred to apply short intense pulses, since this viscosity heating effect is non-linear. Typical parameters may be: pulse length between 10 μsec and 10 msec, more preferred between 100 μsec and 1 msec. The pulse repetition rate is preferably matched to the pulse length to generate a power duty of 1% to 10%. The average power is preferably controlled by peak power and duty, in order to control the heating of tissues. While the basic effect is non-thermal, some increase in temperature may be desired, since it reduces the strength of the cells. Preferably tissue heating above normal body temperature is kept below 44° C., a temperature known as the pain threshold. Controlled tissue heating according to the invention can be obtained from the ultrasound energy, more preferably, RF energy is applied to the treated volume as detailed below.

The pulse width and pulse repetition rates are preferably selected to be as far as possible from those optimal for cavitations at the treated tissues. As disclosed in U.S. Pat. No. 6,113,558, there is an optimal pulse length and pulse repetition frequency for generating cavitations, which are preferably to be avoided. These optimal conditions for cavitations may depend on tissue type and its conditions (such as temperature).

Therefore the specific minimum cavitations conditions may require some matching to the treated site. A cavitations sensor may be included in the system to assist finding the minimum cavitations conditions. Detection of cavitations can be based on the detection of enhanced reflections at the transmitted ultrasound frequency or by the detection of ultrasound radiation at half the transmitted frequency, which is a known indication of cavitations.

The differences in sound velocities between the lipid vacuole and other fluids in the fat tissue are due to differences in compressibility. At elevated temperature, the difference increases. ("Physical properties of tissue", by Francis A. Duck, Academic Press Ltd., 1990, p. 85, FIG. 4.1). For example, the sound velocity at 40° C. for fat and other body fluids is 1400 m/s and 1520 m/s, respectively. The respective adiabatic compressibility values are $\beta=5.6\times10^{-10}$ and $\beta=4.2\times10^{-10}$. Thus, under these conditions, the fat is more compressible than other body fluids by 30%. However, high pressures are required to exploit this. For example, a pressure of P=10 MPa will generate a relative volume changes $\Delta V/V=\beta P=5.6\times10^{-3}$ and $\Delta V/V=\beta P=4.2\times10^{-3}$ for the lipid and cytoplasm respectively. The difference between the fluids is $1.4\times10^{-3}$, which over a scale of typical cell size (50-100 micrometers) will cause a relative movement of about 0.1 µm. For comparison, the mass density difference effect yielded movement of about 0.2 µm at a lower pressure of 4 MPa.

In accordance with one aspect of the invention, at least one ultrasound transducer configured to be applied to a skin surface, radiates ultrasound energy through the skin into the subcutaneous fat layers to effect relative movement between fat cell constituents and to cause fat cell necrosis or apoptosis. According to the invention, a flat transducer having a uniform phase over its surface is used, or a moderately focused transducer with fixed focus, or a phased transducer array, which can produce a moderate focus and can be electronically scanned inside the fat tissue to cover a larger treatment volume.

As explained above, almost all prior art high power ultrasound applications use a very high degree of focusing, to enhance the ratio between the wanted damage at the target tissue and unwanted damage at the entrance layers (between transducer and target). However, since according to the present invention the tuning is for selective damage to fat cells, moderate focusing is used. Moderate focusing can reduce unwanted cavitations effects while not reducing cell rupturing. This is attributed to the fact that cavitations depend on the pressure magnitude of the ultrasound wave (more specifically, on the negative pressure magnitude) and not on the pressure gradient.

In another of its aspects, the invention provides a method and apparatus for delivering ultrasound energy to subcutaneous adipose tissue. According to this aspect of the invention, skin and a region of the underlying adipose tissue are made to protrude out from the surrounding skin surface. Ultrasound energy is then directed to adipose tissue in the protrusion. The protrusion may be formed, for example, by applying a negative pressure (vacuum) to the skin region or by mechanical manipulation of the skin region. The apparatus of this aspect of the invention includes an applicator adapted for causing a skin region to protrude above the surrounding skin region and one or more ultrasound transducers which radiates ultrasound energy preferably into said protrusion.

Creating a protruding region of skin and underlying adipose tissue and radiating the ultrasound energy preferably parallel or close to parallel to the non-protruding skin surface, has the advantage that the radiation is preferentially directed into the fat tissue inside the protrusion while much less ultrasound energy is directed into other body tissues. This reduces the risks of unwanted damage to deep body tissues which might be much more sensitive to ultrasound energy, such as lungs, and reduces the pain which is known to be effected when high intensity ultrasound radiation heats the bones. A preferred apparatus according to the invention may include at least two ultrasound transducers with overlapping irradiated focal volumes inside the adipose tissue. The relative phases of the emitted radiation from said transducers may be controlled for maximizing the pressure gradients at selected locations inside the treated tissue.

In another of its aspects, the present invention provides a method and apparatus for treating subcutaneous adipose tissue. The method comprises directing ultrasound energy and RF energy to the adipose tissue. The apparatus of this aspect of the invention includes an applicator having at least one pair of RF electrodes and at least one ultrasound transducer. Applicant's co-pending U.S. patent application Ser. No. 11/189,129 discloses the combination of high frequency ultrasound energy and RF energy in skin rejuvenation treatments. That application discloses generating a path of higher RF conductivity by heating of selected tissue volume by focused ultrasound, and applying RF to the body which will preferentially flow through the high conductivity path. However the situation with adipose tissue is much more complex, due to the large differences in the mechanical, electrical and thermal properties of the majority lipid vacuole fluid and the minority cytoplasm and intercellular fluids. The total electrical conductivity inside the tissue is composed from direct, Ohmic conductivity of the intercellular fluid, and the Ohmic conductivity of the fluids inside the cells in series with the capacitance of the cell membrane (which is a poor conductor). Since in mature adipose cells, most of the cell volume is filled with the poorly conducting fluid of the lipid vacuole, most of the current flows in the narrow channels of the cytoplasm and the intercellular fluid. Thus, although both RF energy and ultrasound energy are known to be poorly absorbed in fat tissue, most of the absorbed energy goes to the very thin layers of fluids between the lipid vacuoles, which occupy a very small fraction of the fat tissue volume. While on average, a relatively small amount of energy is absorbed in the adipose tissue, the specific energy transferred to the small volumes of cytoplasm and intercellular fluid may be high. The fact that the cell membrane borders these fluids makes the energy investment in these fluids very effective for destruction of the cell membrane, followed by cell necrosis or apoptosis. Selective heating of these fluids can be achieved by exploiting the difference in the cell fluid properties, as discussed above. The RF energy and the ultrasound energy combine in these specific fluids of the fat tissue, so the desired effects are enhanced without increasing the danger of collateral damage which might be produced in other tissues, especially at the skin through which the energy is delivered, if the energy of a single type is increased to obtain the same effect. The combination of ultrasound energy and RF energy is more effective in several ways. The heating of tissue by ultrasound increases the RF conductivity, so that more energy is delivered by the RF, and the total heating reduces the cell strength. In adipose cells, these effects are concentrated mainly in the thin layers of the cytoplasm, so it is more effective for destruction of fat cells and the selectivity is enhanced by the combination. The combination of ultrasound and RF energy also increases the strain on the fat cell membrane, since both ultrasound and RF induce such strain on fat cells. The ultrasound wave generates a strain at the fat cell membranes as discussed above. The electric fields of the RF also generate strain due to charging of the membranes (see, for example, Herve Isambert, Supra). Simultaneous application of RF and ultrasound on the same tissue volume yields a combined strain. In the adipose tissue both effects concentrate at the thin cytoplasm and the adjacent membrane of the adipocytes. That combination may reduce the intensity required from each energy source, so that the risk of collateral damage may be reduced.

In a preferred embodiment of this aspect of the invention, at least one ultrasound transducer and at least two RF electrodes are applied to the protuberance. A region of skin and underlying adipose tissue to be treated is made to protrude above the surrounding skin surface. The RF energy may be applied prior to or during formation of the protuberance to pre-heat the tissue. The RF energy may be applied prior to and/or at least partially simultaneously with the ultrasound energy. When this protrusion is created, the transducers are driven to radiate ultrasound energy into the protruding tissues. RF energy is applied to the tissue via the at least two electrodes, which are either conductive for direct injection of current to the skin, or insulted by a thin layer of insulating material for capacitive coupling of energy to the tissue.

Application of RF and ultrasound energies to a protruding region of skin allows treatment of subcutaneous adipose tissue and cellulites.

DETAILED DESCRIPTION OF PREFERRED EMBODIMENTS OF THE INVENTION

Figure 2:
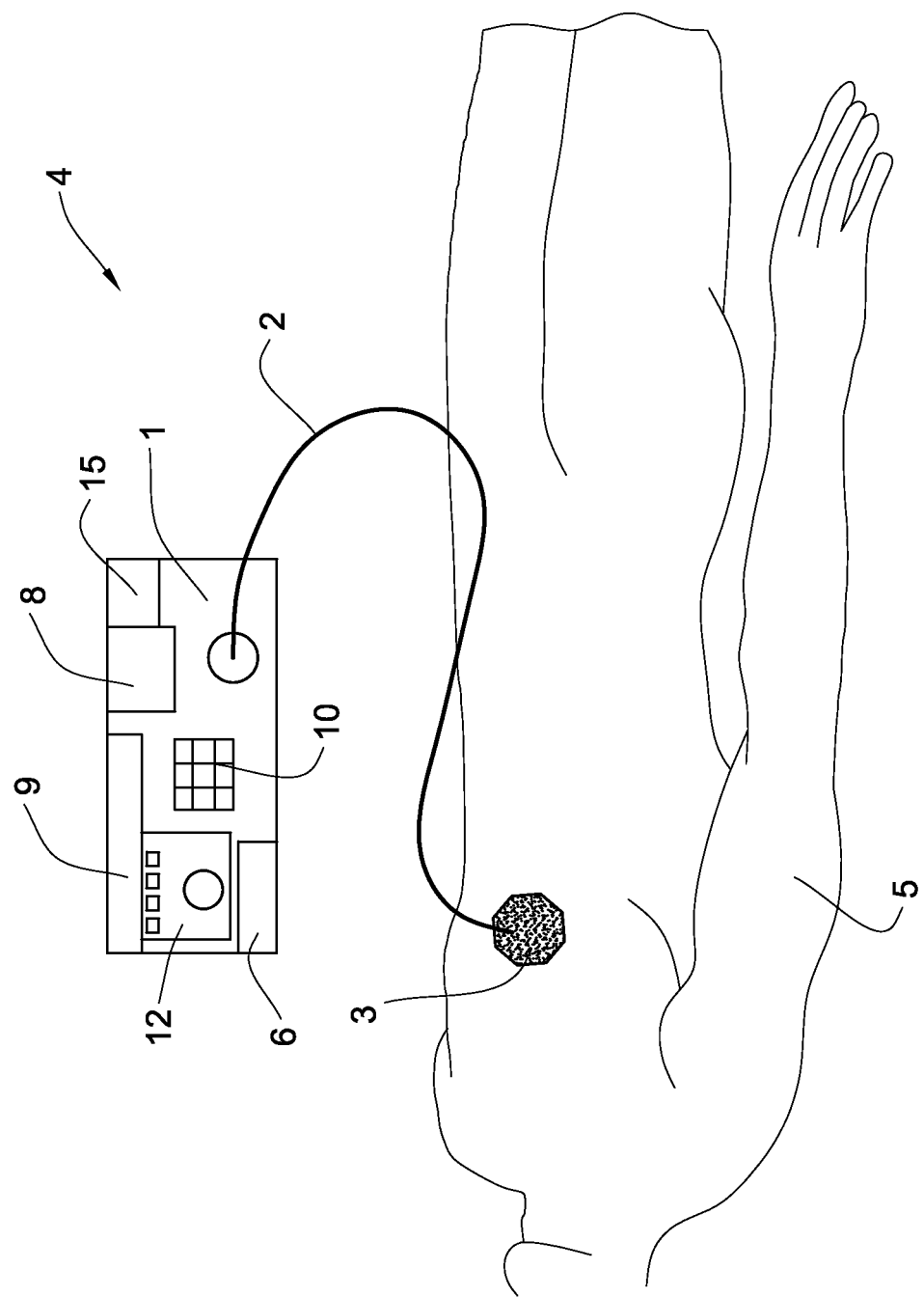
FIG. 2 shows an apparatus 4 for reduction of adipose tissue in accordance with one embodiment of the invention.

FIG. 2 shows an apparatus 4 for applying ultrasound to subcutaneous adipose tissue in accordance with one embodiment of the invention. An applicator 3, to be described in detail below, contains one or more ultrasound transducers. The applicator is adapted to be applied to the skin of an individual 5 in a region of skin and underlying adipose tissue to be treated. The applicator 3 is connected to a control unit 1 via a harness 2. The control unit 1 includes a power source 8. The power source 8 is connected to an ultrasound driver 6. The control unit 1 contains a processor 9 for monitoring and controlling various functions of the system. The control unit 1 has an input device, such as a keypad 10 that allows an operator to input to the processor 9 selected values of parameters of the treatment, such as the frequency, pulse duration and intensity of the ultrasound energy to be directed to the adipose tissue.

The applicator 3 may optionally contain one or more pairs of RF electrodes in addition to the ultrasound transducers. In this case, the power supply 8 is connected to an RF generator 15 that is connected to the RF electrodes in the applicator 3 via wires in the cable 2. When RF electrodes are included in the applicator 3, the processor 9 may monitor the electrical impedance between electrodes and determined the temperature distribution in the vicinity of the target from the impedance measurements. The system 1 may optionally includes cooling means for cooling the skin surface during treatment. For example, the control unit may contain a refrigeration unit 12 that cools a fluid such as ethanol or water for cooling the applicator 3. The cooled fluid flows from the refrigeration unit 12 to the applicator via a first tube in the harness 2, and flows from the applicator 3 back to the refrigeration unit via a second tube in the harness 2.

The control unit may also include a vacuum pump 18 for evacuating an interior chamber in the applicator 3, in order to cause a region of the skin surface to protrude above the surround surface. The pump 18 is connected to an interior chamber of the applicator 3 by a vacuum hose in the cable 2, as explained below.

In accordance with one aspect of the invention, the applicator 3 is configured to deliver ultrasound energy to a region of subcutaneous adipose tissue that so as to generate a pressure gradient in the region that ruptures selectively fat cells in the in the region.

Figure 3:
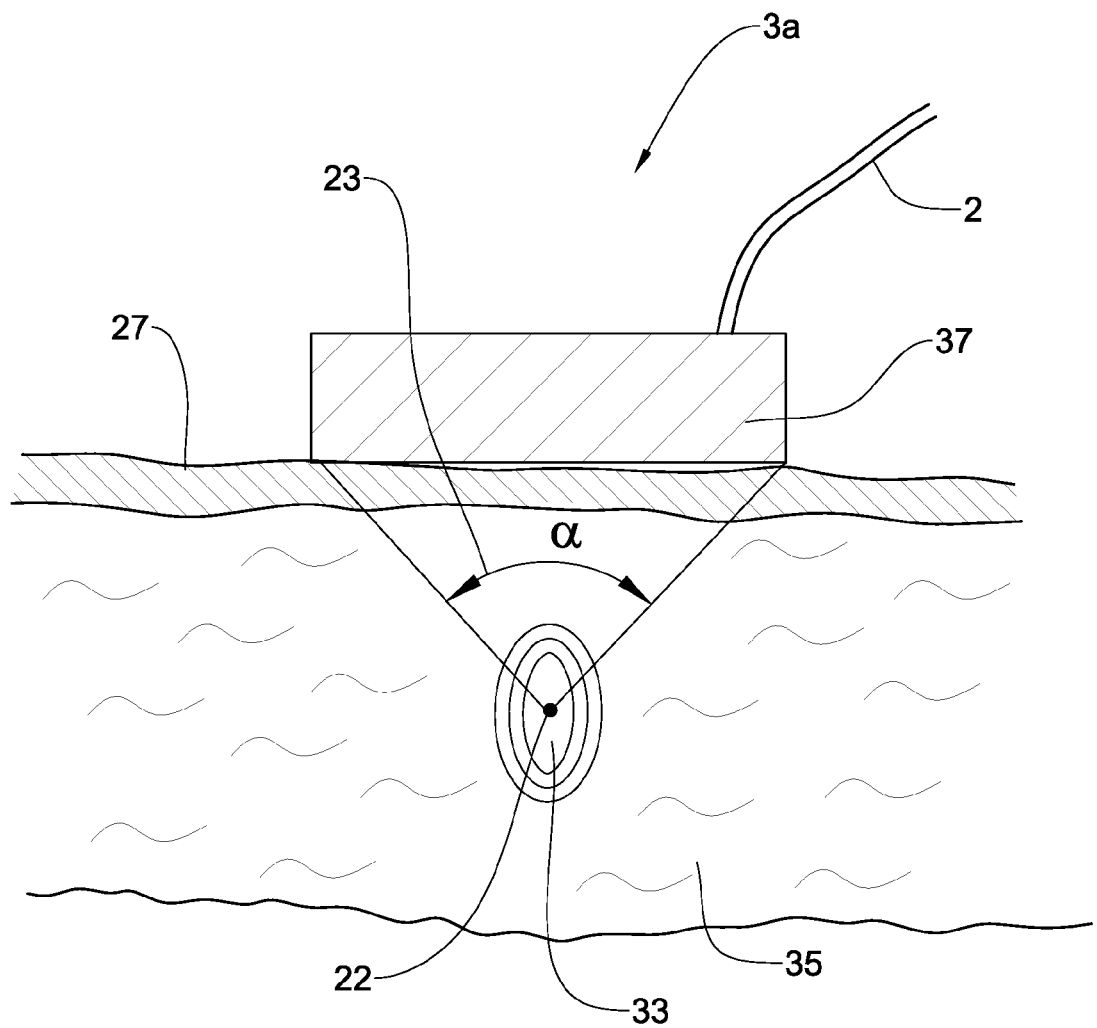
FIG. 3 shows an applicator, including an ultrasound transducer for use in the system of FIG. 1.

FIG. 3 shows an embodiment 3a of the applicator 3. The applicator 3a includes at least one ultrasound transducer 37. The transducer is connected through a cable, preferably a coaxial cable in the harness 2 to the ultrasound driver 6 in the control unit 1. In use, the ultrasound transducer is attached to the skin surface 27, preferably with ultrasound gel or other ultrasound transmitting material, and generates a focal volume 33 extending around focal point 22 inside the subcutaneous adipose tissue 35.

According to one aspect of the invention, the view angle a 23 is limited to maximize the ratio of pressure gradient to pressure at the focal volume. Preferred values are $\alpha < 120°$, more preferred $\alpha < 90°$. The control unit 1 drives the ultrasound transducer at an intensity which produces at the focal volume pressure gradient between 0.5 GPa/m to 50 GPa/m, more preferred between 2 GPa/m to 15 GPa/m. Preferably, the ultrasound radiation is at a frequency lower than 1 MHz, more preferred below 300 kHz. Pulsed operation of the transducer is preferred, preferred pulse lengths between 10 μsec and 10 msec, more preferred between 100 μsec and 1 msec. The pulse repetition rate is preferably matched to the pulse length to generate a power duty of 1% to 10%.

Figure 4A:
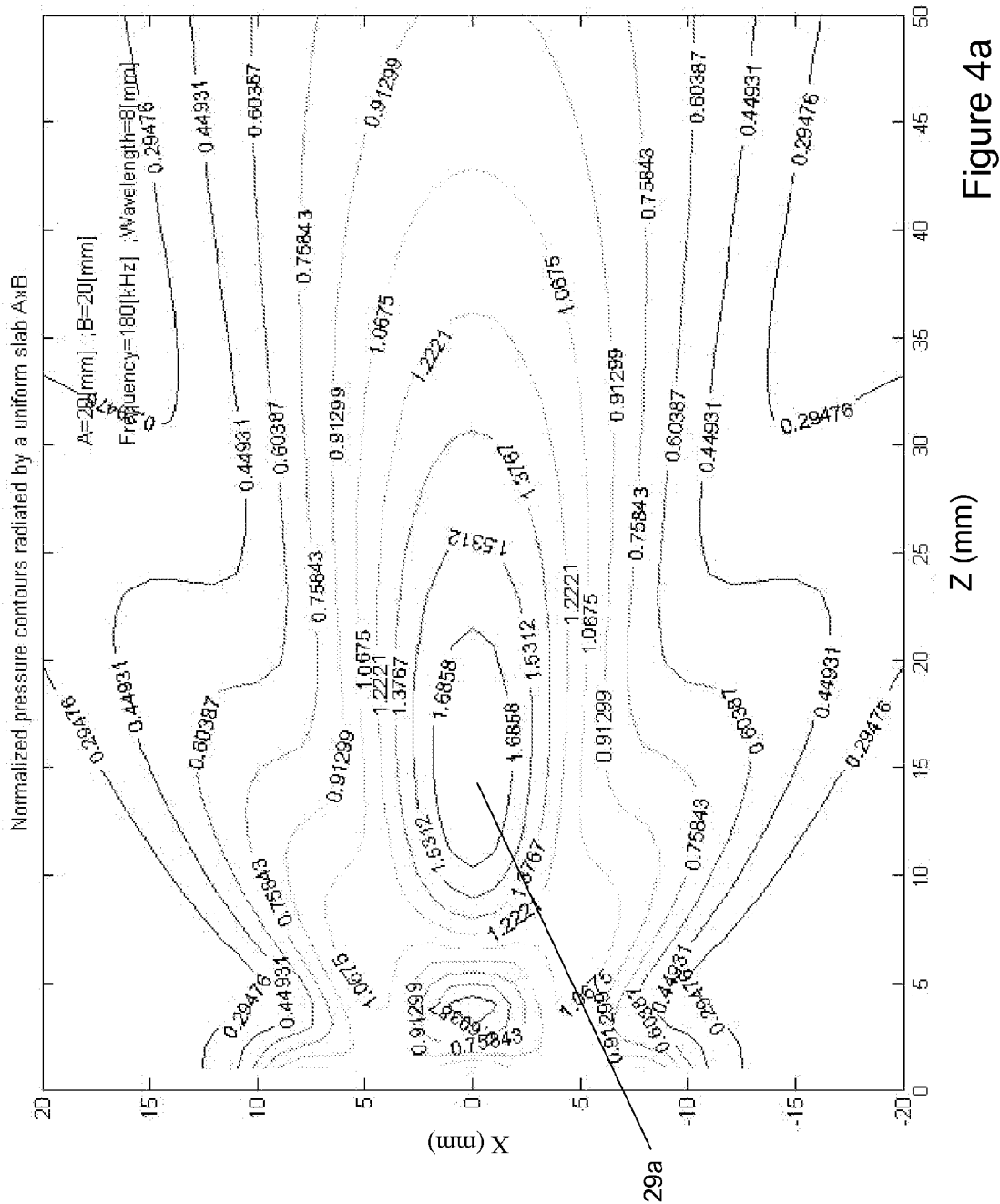
FIGS. 4a and 4b show pressure distribution contours generated by a flat, uniform phase ultrasound transducer.
Figure 4B:
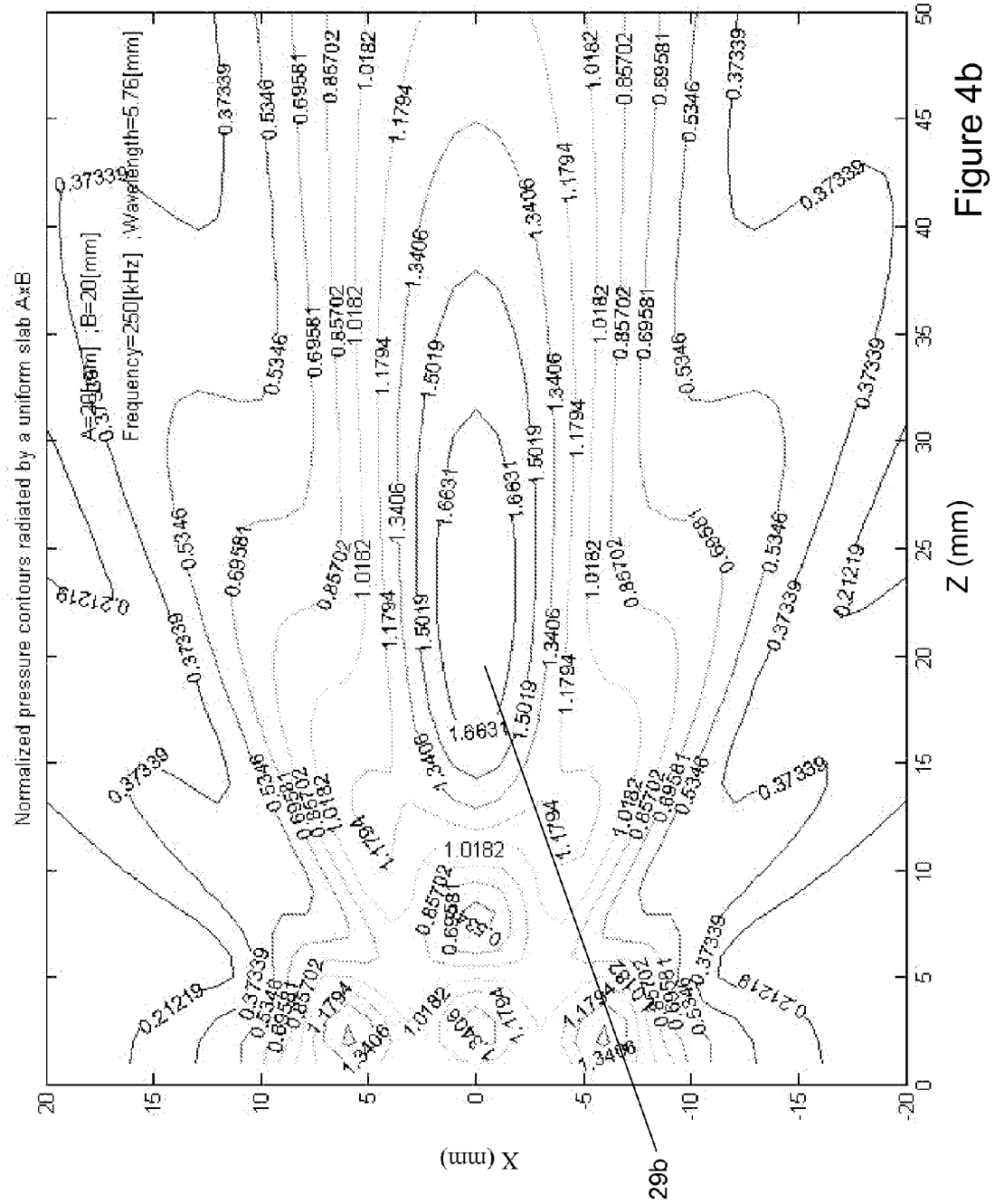

The ultrasound transducer of the embodiments 3a may be flat with uniform phase over its radiating surface. This embodiment has the advantage of simplicity both of the transducer and the driving electronics. A flat, uniform phase transducer generates a pressure distribution, which has a maximum at a focal region, where the pressure can reach more than 1.5 times that on the transducer surface. FIG. 4 shows a specific example for a flat transducer with a 20×20 mm radiating area. In the diagrams of FIG. 4, the x-axis is parallel to the transducer surface while the z-axis is normal to the transducer surface. The origin is at the center of the transducer. Dimensions are in mm. FIG. 4(a) is calculated for ultrasound frequency of 180 kHz, and 4(b) for 250 kHz. The contour numbers are pressures, normalized to a unit pressure on the transducer surface. Since the focusing is very small, contours of pressure gradients at the focal region (not shown) are very close to the pressure contours. The choice of the ultrasound frequency controls the distance from the transducer face to the maxima, and which thus determines the depth of treatment. In FIG. 4(a), the region 29a of maximum pressure has an amplitude of 1.68, and is located between z=10 mm to z=20 mm. For a frequency of 250 kHz with the same radiating area, the maximum pressure is 1.66 and moves to a region 29b between z=16 mm and z=32 mm, further from the transducer face, as shown in FIG. 4(b). It is also preferred to select the thickness of the layer between the radiating surface and the skin so that the skin surface is at a region of minimum of radiation intensity. Human skin is typically 1.5-2.5 mm thick. Referring again to FIG. 4(a), contours of minimum pressure are at a distance of up to about 4 mm from the radiating surface. By coating the transducer face with a layer of material having acoustical impedance close to that of human tissues and having a thickness of about 4 mm, a ratio of about 1.66 between the maximum pressure in the subcutaneous adipose tissue and maximum pressure at the skin is obtained.

A curved transducer and/or transducer with a lens which produces stronger fixed focusing can be applied according to the invention. Another embodiment will have the transducer 37 made as a phased array, with a multi-channel phased driver in the control unit 1. An example of a phased array ultrasound system, with a detailed description of high intensity phased array technology as known in the art, can be found in the paper by K. Y. Saleh and N. B. Smith, Int. J. Hyperthermia Vol. 20, NO. 1 (Feb. 2004), pp. 7-31. An apparatus based on a phased array is more complicated both in the transducer and in the driving electronics. However it has the following advantages:

a. Control of degree of focusing.

b. Control of depth and position of focal volume.

c. Possible scanning of focal volume inside a selected volume of tissue.

At least one element of the array, or any additional small transducer in the non-array embodiments, may be a sensor comprising a receiver that is tuned to half the transmitting frequency to detect generation of cavitations in the body tissue, and/or tuned to the transmitted frequency to detect enhanced reflectivity from hard body tissue or from cavitations. According to the output of this sensor, the control unit 1 varies the radiated ultrasound properties (pulse length, repetition rate and intensity) to minimize their unwanted effects. A phased array embodiment also enables positioning the focal volume away from the hard tissue and/or reducing the focusing to reduce cavitations.

The embodiment 3a of the applicator has the advantage of simplicity, however, since focusing is limited, there is a risk that residual ultrasound energy will enter deeper into the body and hit sensitive tissue such as lungs and effect unwanted damage. Also, if this residual ultrasound energy were to hit bones, it might cause pain. To reduce these risks, the embodiments 3b to 3g may be used. These embodiments exploit the very high flexibility of fat tissue, and based on generating a protrusion out of the body surface and attaching at least one ultrasound transducer to that protrusion. This transducer radiates preferably in a direction parallel to the undisturbed body surface, or at least as close as possible to that optimal angle. Under these conditions, the adipose tissue inside the protrusion is exposed preferentially, while much less radiation arrives at deeper body tissue. These embodiments can be based on mechanical manipulations and/or on application of negative pressure (vacuum) as detailed below.

Figure 5:
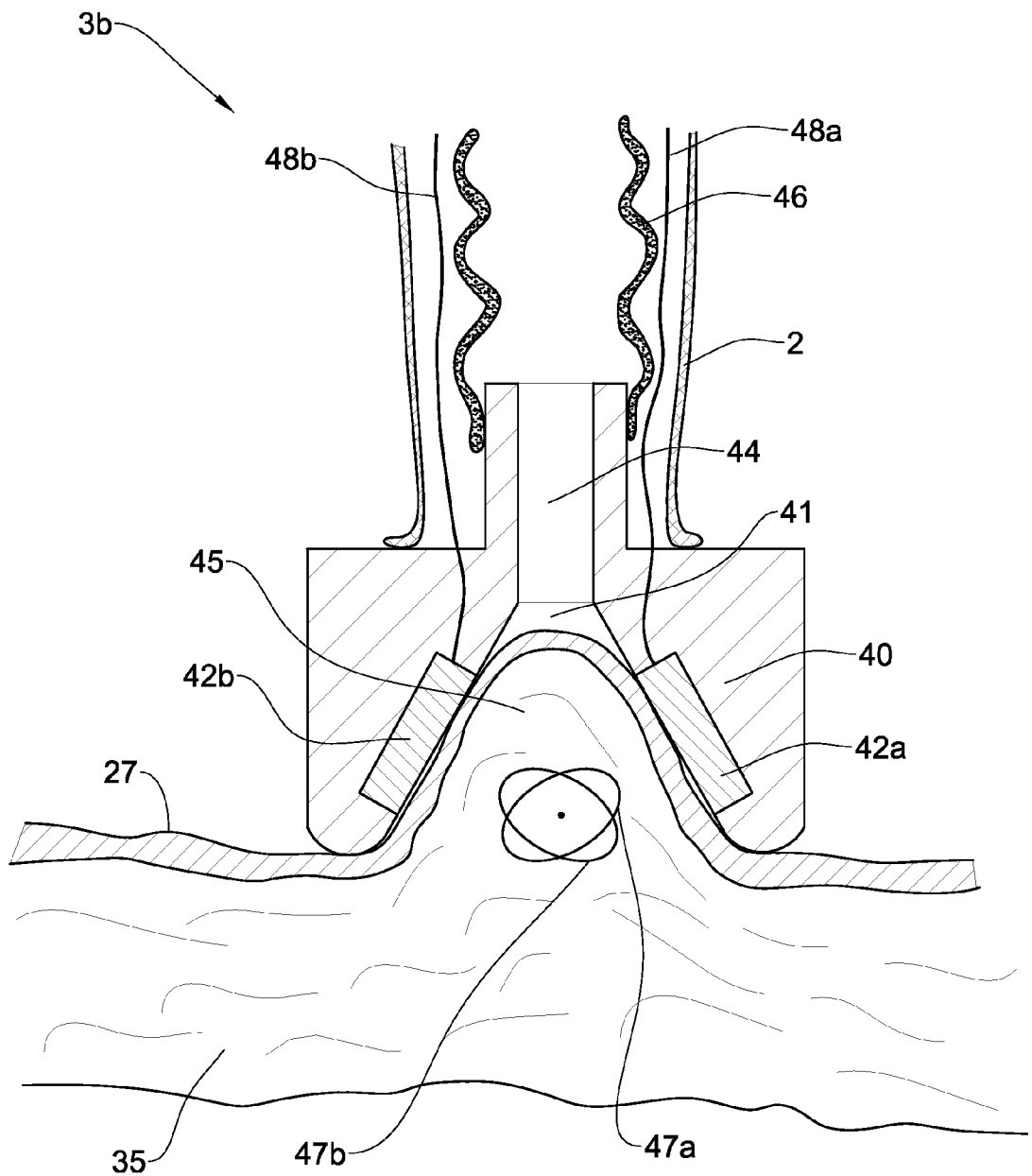
FIG. 5 shows an applicator configured to radiate ultrasound energy into a body protrusion created by negative pressure.

FIG. 5 shows the embodiment 3b of the applicator 3. The applicator 3b is shown in cross-section in FIG. 5 and includes a hollow dome 40 having an interior chamber 41. At least one ultrasound transducer 42a and possibly more transducers, such as 42b, are located in the interior chamber 41. The dome 40 is applied to the skin and a negative pressure is generated in the interior chamber 41 by pumping the air out through port 44 by the vacuum pump 18 located in the control unit 1 that is connected to the interior chamber by a vacuum hose 46 in the harness 2. Due to the negative pressure, body tissue 45 including skin and subcutaneous tissue 35, is sucked into volume 41, thus protruding above the surrounding skin surface. This suction applies the skin surface onto the ultrasound transducers 42a and 42b. The transducers are connected through cables 48a and 48b in the harness 2 to the ultrasound driver 6 in the control unit 1. The cables may include coaxial cables for driving the transducers and optionally for sending output signals from sensors located in the applicator 3b, such as temperature sensors or ultrasound sensors, to the processor 9 in the control unit 1 for processing by the processor 9.

The ultrasound transducers 42a and 42b have focal volumes 47a and 47b located preferably in the protruding portion of the adipose tissue layer 35. The ultrasound transducer may be of any type described above for embodiment 3a. A flat, uniform phase transducer, having the radiation pattern as detailed in FIG. 4, is applied with proper selection of dimensions and frequency to obtain maximum intensity inside the adipose tissue at the protrusion. Any fixed focus transducer can also be applied with the focal volume preferably at that region. According to a preferred embodiment, the transducer 42a (and also 42b if included) will be a phased array as described for applicator 3a. The phased array will either focus the radiation at the optimal region of the protrusion, or scan the adipose tissue inside the protrusion. Although phased array is more complicated, it has the advantages of optimal delivery of energy into the adipose tissue at the protrusion with minimal residual energy going to other tissues.

In a preferred embodiment, at least two transducers 42a, 42b are used so that their volumes of maximum intensity 47a and 47b overlap. Preferably the phases of the transducers are controlled, and matched in a way that maximizes the ultrasound intensity in the overlapping volumes or to maximize the pressure gradients there. The transducer 42a (and the transducer 42b and as well as any other transducers when present) is preferably oriented in the interior chamber 41 so that the direction of ultrasound radiation from the transducer is close to being parallel to the skin surface outside the protrusion. In this orientation, penetration of the ultrasound energy to internal tissues and organs below the subcutaneous adipose layer is reduced or eliminated. Another embodiment will create this preferred direction of radiation by building a transducer which radiates at an angle to its surface. That angle can be fixed and produced by inserting a material with appropriate sound velocity in front of the transducer, or by a variable radiation angle from a phased array, controlled by unit 1.

A pressure sensor may be included inside the interior chamber 41. In this case, the control unit 1 may be configured to drive the ultrasound transducers 42a and 42b when the measured pressure is within a predetermined range. The propagation of ultrasound radiation from the transducer into the tissue can be monitored by measuring the electrical impedance of the transducer, that is, by measuring the AC voltage and current on the transducer. Variations in power transmission from the transducer are manifested by changes in the voltage-current relation on the transducer.

The radiating area of each of the transducers 42a and 42b may be, for example, between 5×5 mm to 50×50 mm, more preferably between 10×20 mm to 20×40 mm, depending on the volume of tissue to be treated.

Figure 6:
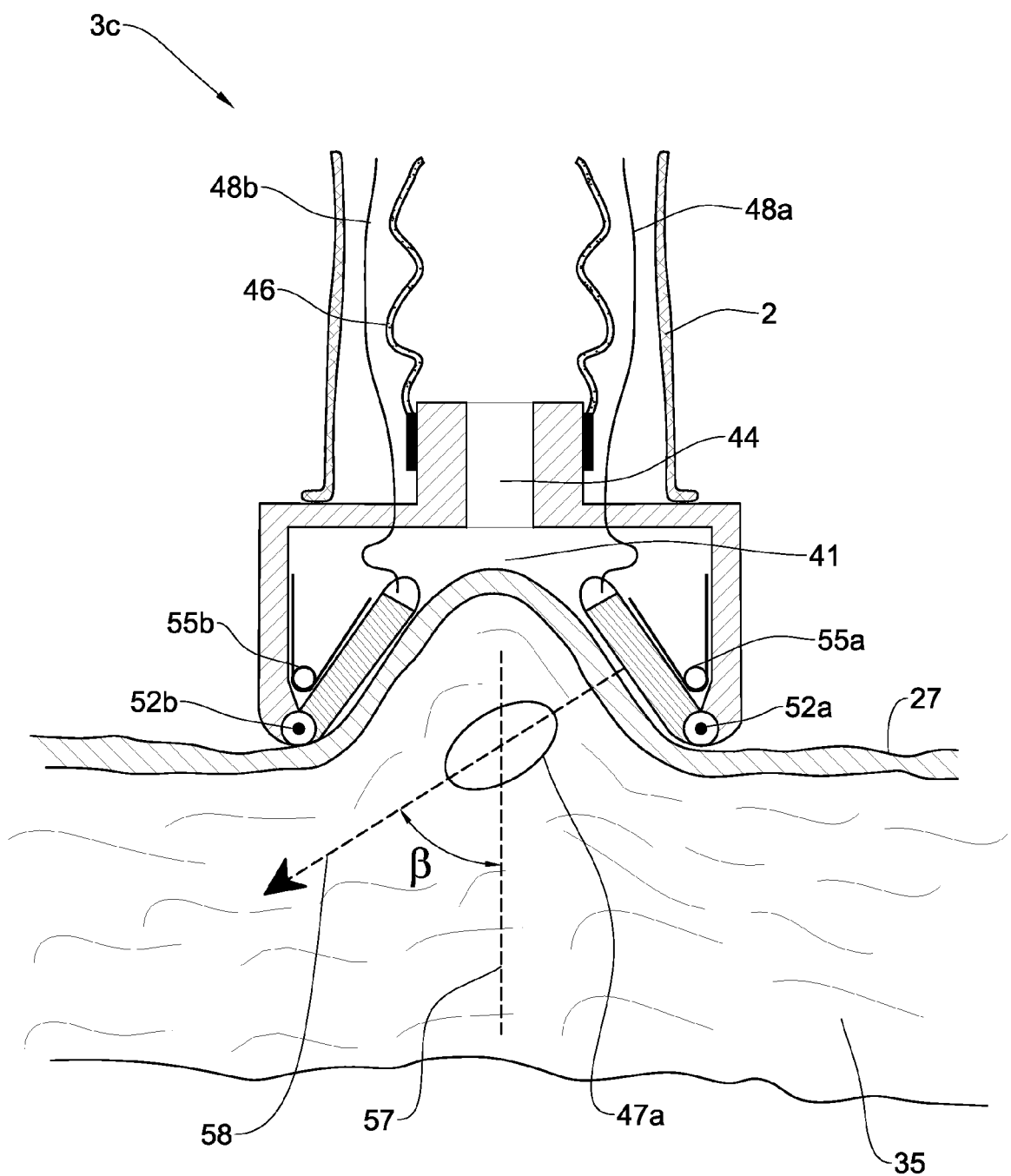
FIG. 6 shows the applicator of FIG. 5 provided with degree of freedom for the ultrasound transducer to rotate and adapt to the protrusion.

FIG. 6 shows an embodiment 3c of the applicator 3 in which the transducers 42a and 42b are allowed a degree of freedom so that they can acquire an orientation that conforms to the skin surface in the protrusion. In the embodiment of FIG. 6, at least one ultrasound transducer, or the two ultrasound transducers 42a and 42b are mounted on hinges 52a and 52b respectively, and displaced towards the center by respective springs 55a and 55b. The electrical cables 48a and, 48b are flexible, so that the transducers are free to rotate about the hinges 52a and 52b. Negative pressure is created inside the interior chamber 41 as explained above with reference to FIG. 5. As the tissue is sucked into the interior chamber 41, it pushes the transducers 42a and 42b against the force of springs 55a and 55b, thus causing them to rotate on the hinges 52a and 52b against the force of the springs 55a and 55b. The direction of maximum acoustical radiation (beam direction) of the transducer 42a is indicated in FIG. 6 by ray 58, creating an angle β with the normal 57 to the non-protruding skin surface. As explained above with reference to FIG. 5, the angle β is preferably as close as possible to 90° (i.e. the radiation is close to being parallel to the non-protruding skin surface). In embodiment 3c, the angle β depends on the properties of the tissues at the treatment site and on the controllable parameters, such as the negative pressure amplitude, its application time and the spring constants of the springs 55a and 55b. The closer the angle β is to 90°, the lower the amount of energy that traverses the adipose tissue 35 and enters other tissues deeper inside the body.

The ultrasound transducer(s) of embodiment 3c can be any of those applicable to embodiment 3a and 3b. When a phased array is used, the phase of each element is controlled by an electronic driving circuit in the control unit 1, so that the focal volume can be aimed easily by the electronic control of the array at a desired region inside the adipose tissue. When the transducers 42a and 42b in the embodiment 3c of the applicator 3 are phased arrays, an angle encoder can be associated with each of the hinges 52a and 52b to determine the orientation of the transducers 42a and 42b. The desired focal point can then be determined according to their orientation, and the control unit 1 will phase the array to bring the focal volume to that position inside the fat tissue. The time scale of vacuum pumping is between 50 msec and 1 sec, which is also the time scale of variation of the angles of the transducers, while the focal point can be shifted within a few tens of microseconds to the desired location. Another important advantage of a phased array is the ability to scan a selected volume within the adipose tissue, by electronically controlling the phase of the array elements. The electronic scanning is fast, and can cover a large volume within the typical pumping time. Also, the degree of focusing can be controlled by the electronics.

In another embodiment, the generation of the protrusion of skin and underlying adipose tissue is done by mechanical manipulation of the skin surface. This embodiment avoids the need to vacuum system as is required when the protrusion is formed by negative pressure.

FIG. 7 shows an example of an embodiment 3d of the applicator 3 which delivers a mechanical manipulation of a skin surface in order to generate a protruding region of skin tissue and underlying adipose tissue. The applicator 3d includes a base element 300, which may be connected to a handle (not shown). Grooves 301 and 302 are provided inside the base element 300 in which bars 303 and 304, respectively, can move laterally. Rods 305 are 306 are attached to the bars 303 and 304, respectively. Plates 307 and 308 are connected to the lower end of the rods 305 are 306, respectively. The lower surface of these plates is preferably rough or covered with a suitable high-friction material 309 in order to enhance friction and reduce slippage over the skin. Ultrasound transducers 311 and 312 are attached to plates 307 and 308 respectively through hinges 313 and 314 respectively so as to be free to rotate about the hinges. The springs 315 and 316 displace the transducers, 311 and 312, respectively towards the skin surface 27. At the upper end of the rods 305 and 306, rods 317 and 318, respectively, are connected. The rods 317 and 318 are driven by an actuator 319.

The embodiment 3d has two ultrasound transducers, arranged symmetrically. This is by way of example only and a non-symmetrical mechanical manipulator with only one transducer or more than two transducers may be used as required in any application.

Figure 7A:
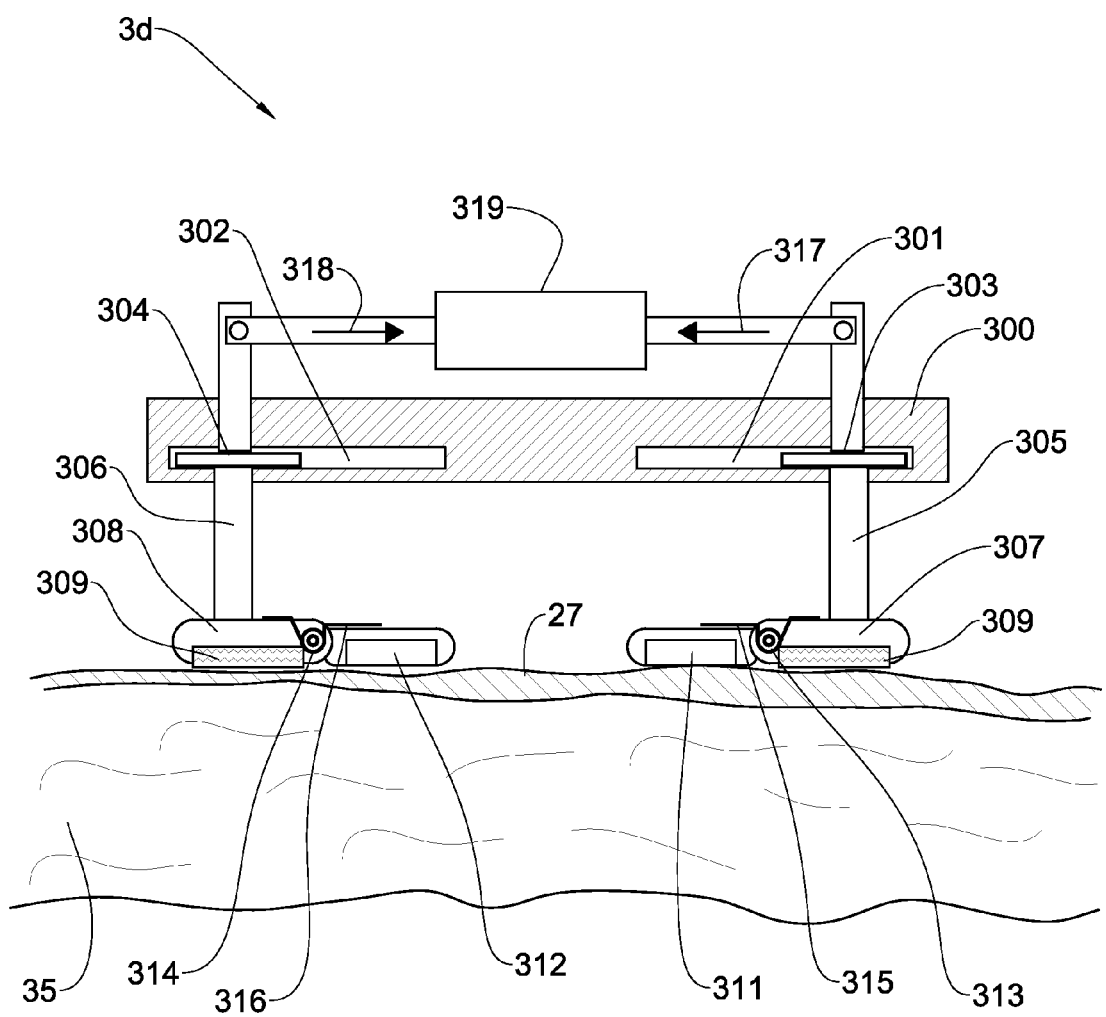
FIGS. 7a and 7b show an applicator configured to radiate ultrasound energy into a body protrusion created by mechanical manipulation of the skin.
Figure 7B:
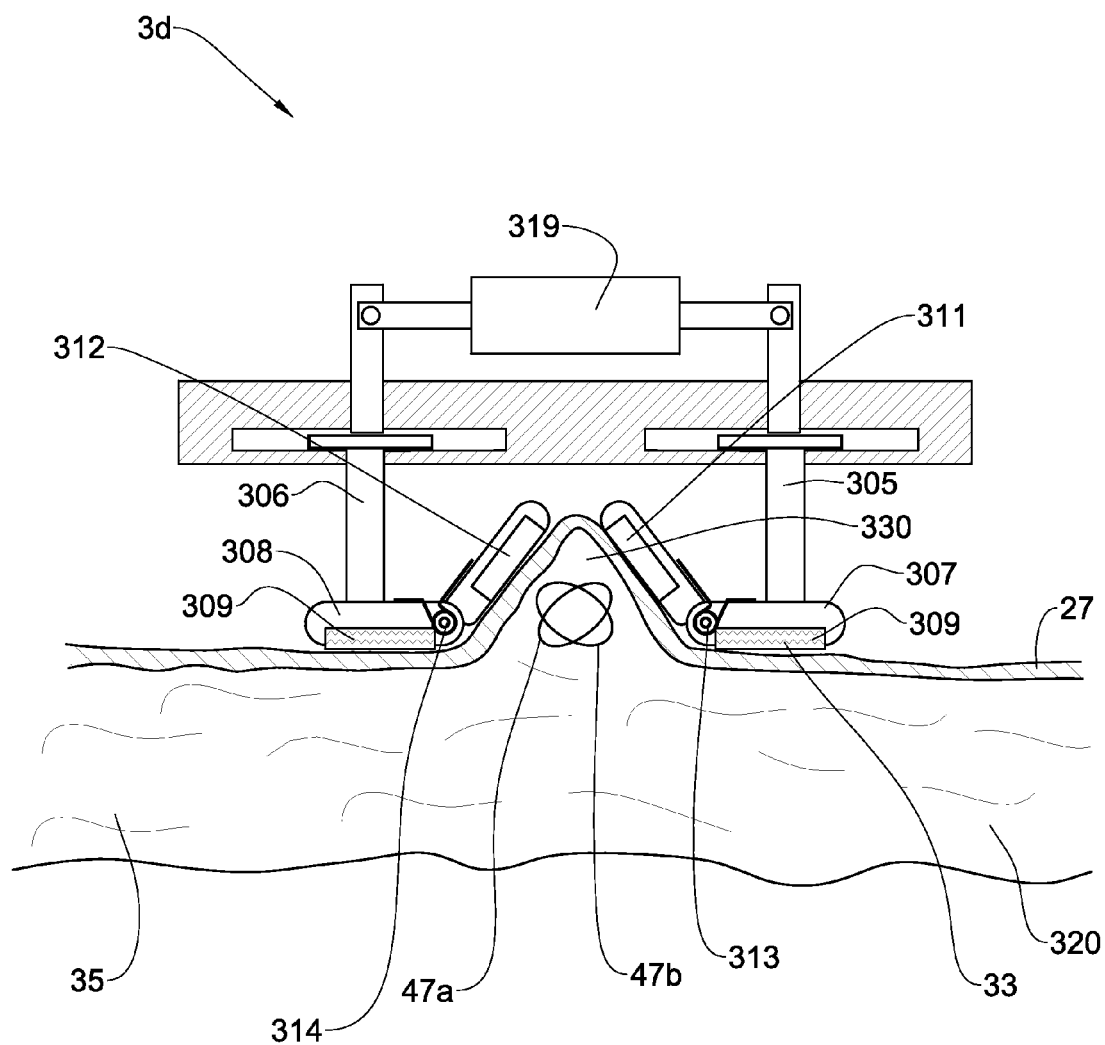

The embodiment 3d of the applicator 3 is used to create a protrusion of a skin surface as follows. The plates 309 and 310 are applied onto the skin surface 27 at a site to be treated, as shown in FIG. 7a. The actuator 319 pulls the rods 305 and 306 inwards together with the plates 307 and 308 and the transducers 311 and 312. As shown in FIG. 7b, due to the high coefficient of friction between the layer 309 and the skin surface, the body tissue 320 is pushed upwards so as to form a protrusion 330. The springs 313 and 314 are designed so that the moment they exert on the transducers 311 and 312 is low enough to allow the transducers to rotate about the hinges 313 and 314, respectively, so as to allow formation of the protrusion, while at the same time, ensuring good coupling of ultrasound energy from the transducers 311 and 312 to the skin surface 27. After the protrusion has been formed, the transducers 311 and 312 radiate ultrasound energy into the body tissue, to effect reduction of the fat in focal volumes 47a and 47b in the subcutaneous adipose tissue 35. The ultrasound transducers may be contained inside the plates 307 and 308. In this case, it is desirable to allow a degree of freedom of movement to these plates, so as to allow them to conform to the protrusion as it forms, either freely, or by forcing them to rotate simultaneously with the lateral motion.

The plates 307 and 306 and/or the transducers 311 and 312 may be curved in any desired shape in order to obtain a protrusion having a desired shape. The transducers 311 and 312 of the embodiment 3d may be any of those applicable for the other embodiments, 3a-3c, that is, planar transducers, fixed focus transducers or phased array transducers. If a phased array is used, in a similar way to embodiment 3c (FIG. 6), a position encoder is preferably added to hinges 313 and 314, and the focal position electronically matched to the orientation of the transducers.

The apparatus 4, with the applicator 3b or 3c or 3d, may be configured to deliver ultrasound energy to a region of subcutaneous adipose tissue so as to generate a pressure gradient in the region that ruptures cells in the in the region. Since this effect is obtained using moderate focusing of the ultrasound radiation in a volume of subcutaneous adipose tissue to be treated, when the overlying skin surface is made to protrude above the surrounding surface, a larger power may be applied with lower risk to internal organs and tissues.

Figure 8:
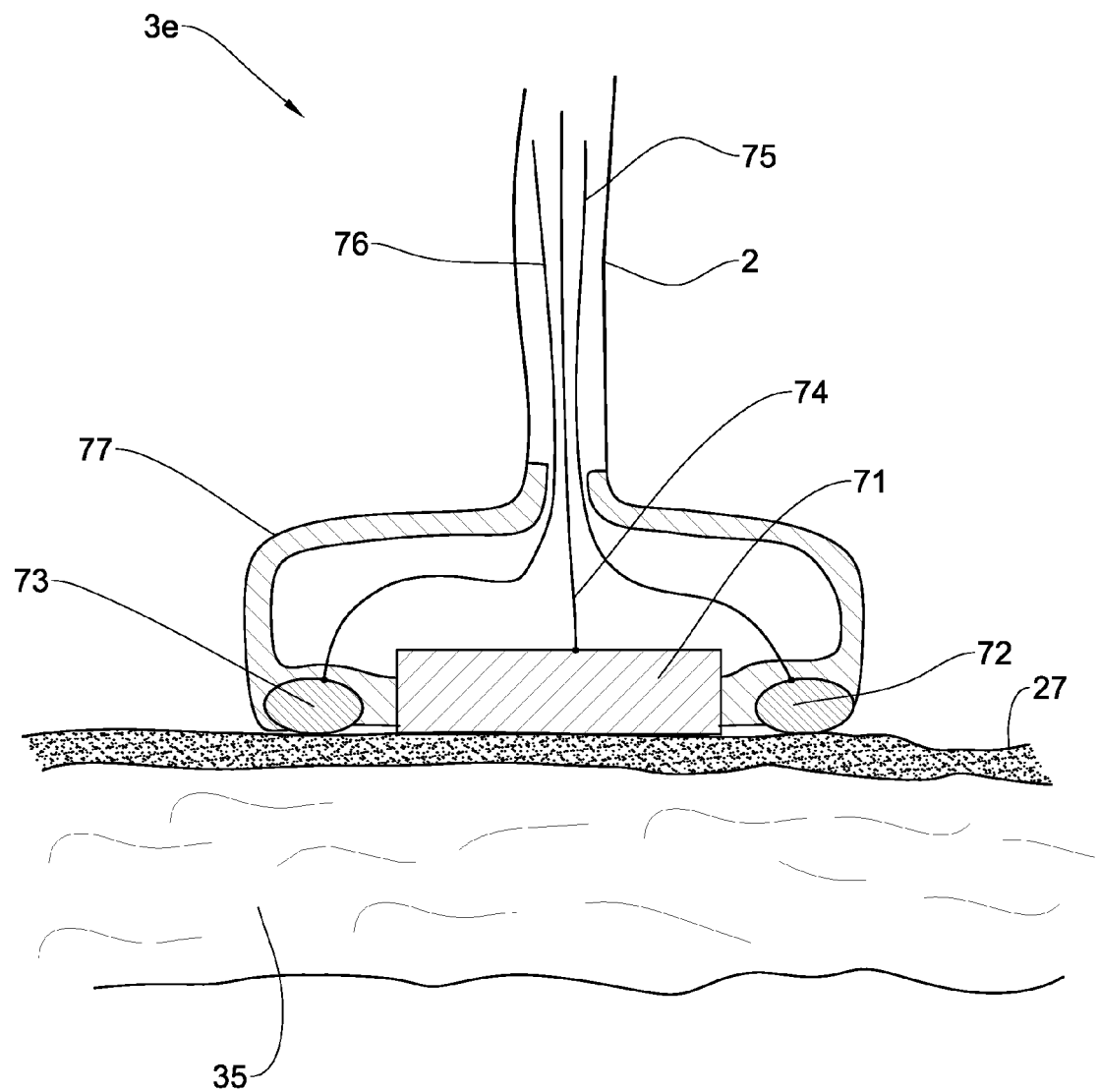
FIG. 8 shows an applicator, including at least one ultrasound transducer and at least a pair of RF electrodes.

Ultrasound energy may be delivered to the skin together with RF energy; as explained above. FIG. 8 shows schematically an embodiment 3e of the applicator 3 in which an ultrasound transducer 71 is located between two RF electrodes 72 and 73. The transducer and RF electrodes are supported by an insulating housing 77. Application of the applicator 3e to the skin surface 27, applies both the ultrasound transducer 71 and the RF electrodes 72 and 73 to the skin surface 27, to obtain good coupling of the RF and ultrasound energies to the skin surface. An electrically conductive ultrasound conductive gel may be applied to the skin prior to the treatment. The ultrasound transducer is driven through cable 74 in the harness 2, while cables 75 and 76 supply the RF voltage to the electrodes from the RF generator 15 in the control unit 1.

Figure 9:
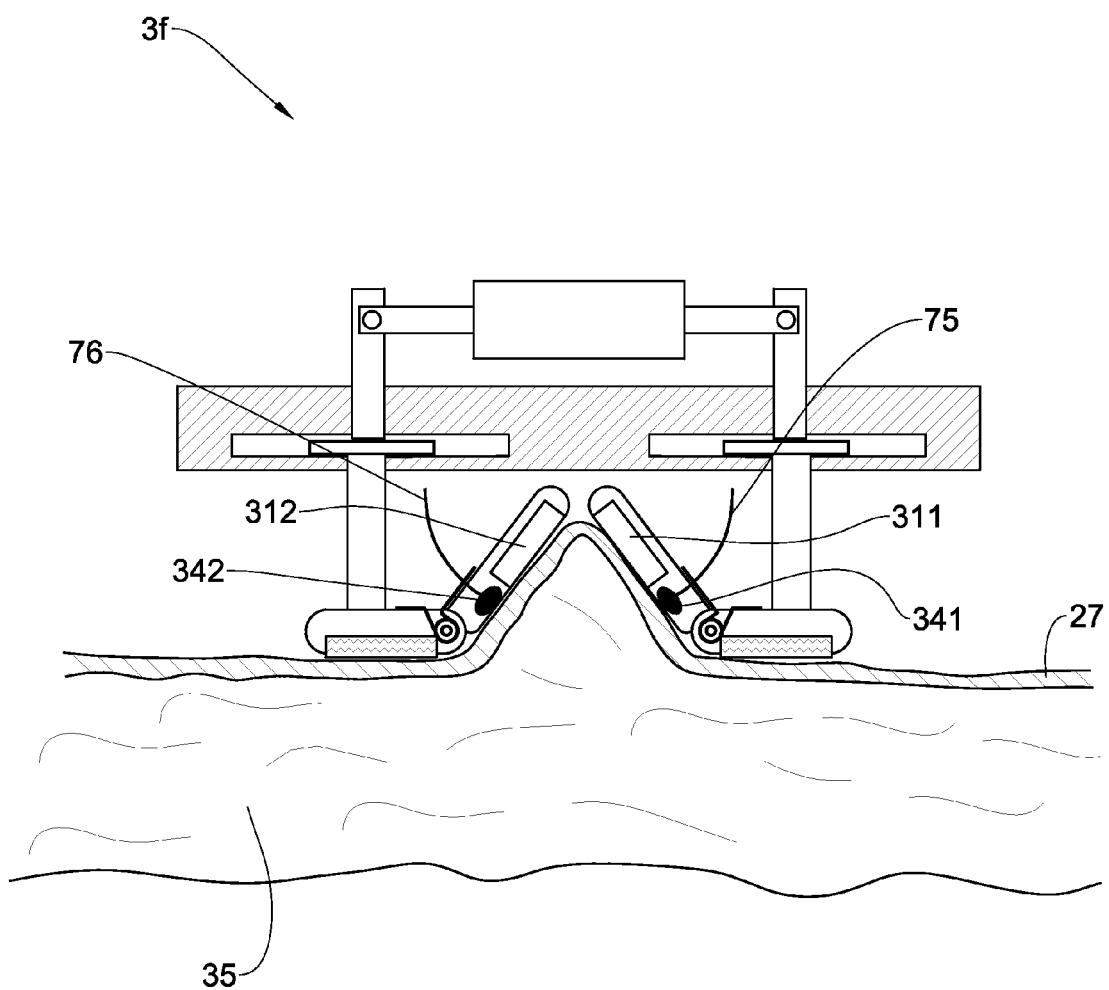
FIG. 9 shows an applicator including at least one ultrasound transducer and at least a pair of RF electrodes configured to provide RF and ultrasound energy into adipose tissue at a protrusion created by mechanical manipulation of the skin.

FIG. 9 shows an embodiment 3f of the applicator 3 in which RF electrodes have been incorporated into the embodiment 3d of FIG. 7. For example, in FIG. 9, RF electrodes 341 and 342 are located adjacent to the transducers 311 and 312. The RF electrodes are driven through cables 75 and 76, which are included in harness 2 (not shown). The RF electrodes can be incorporated into the plates 307 and 308 or on the transducers 311 and 312. In the later embodiment, a thin film of electrically conducting material having negligible ultrasound attenuation is preferably applied to each transducer face touching the skin 27, and connected to the RF power supply 15 in control unit 1.

Figure 10:
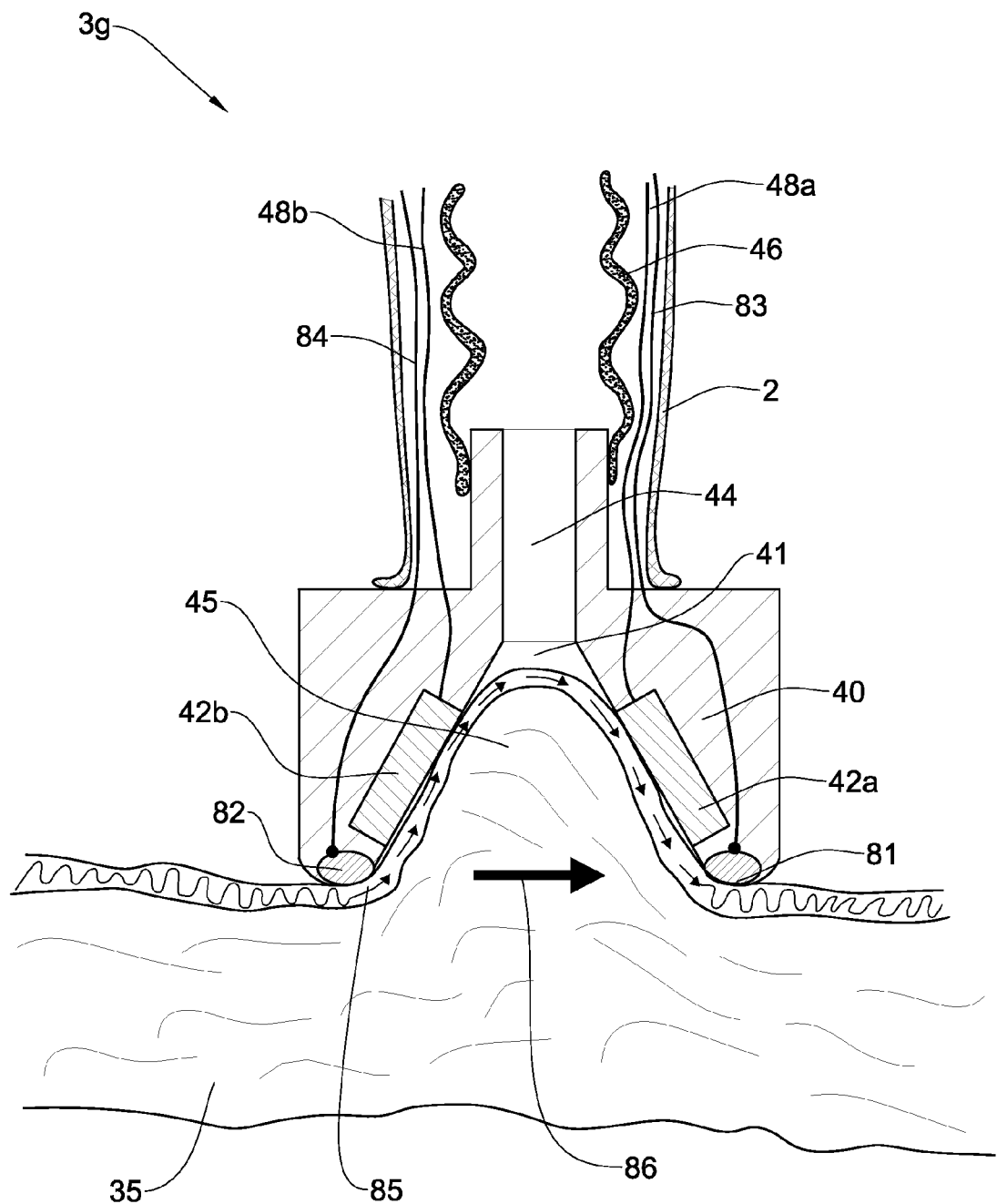
FIG. 10 shows an applicator including at least one ultrasound transducer and at least a pair of RF electrodes, configured to provide RF and ultrasound energy into the adipose tissue at a protrusion created by negative pressure (vacuum)

FIG. 10 shows another embodiment 3g of the applicator 3 in which a pair of RF electrodes 81 and 82 has been added to the embodiment 3b of FIG. 5. The RF electrodes 81 and 82 are located at the sides of the dome 40, so they can contact the skin. The RF electrodes 81 and 82 are driven by the RF driver 15 in the control unit 1 by cables 83 and 84 in the harness 2. The electrodes 81 and 82 and the cables 83 and 84 are electrically insulated from the housing and from the ultrasound transducers. The housing 40 is preferably made of insulating material. The high conductivity contour through the skin layer 85 is longer and takes less energy than in the planar embodiment 3e shown FIG. 8, so a higher electric field 86 is created in the deep adipose tissue. The electric field heats the minority fluids in the adipose tissue and generates strain on the adipose tissue cell membranes, as explained above. Preferably the applicators 3f and 3g are designed to make the regions of maximum electric field and maximum ultrasound intensity at least partially overlaps within the adipose tissue, to maximize the combined effects of the RF and the ultrasound energies. A pair of RF electrodes can similarly be added to applicator 3c.

Figure 11A:
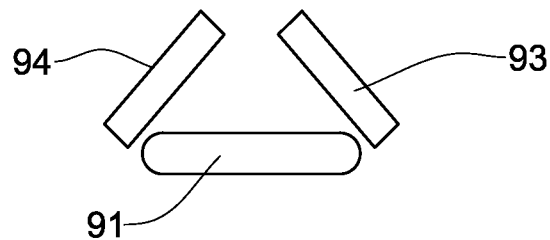
FIG. 11 shows schematically an alternative arrangement of the for RF electrodes with respect to the ultrasound transducers.
Figure 11B:
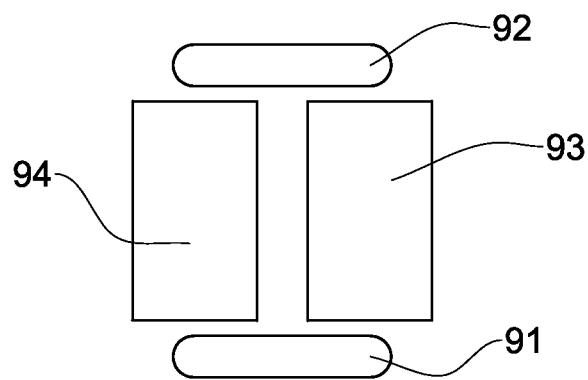

The applicator 3g has RF electrodes parallel to the ultrasound transducers. It is also possible according to the invention to locate the RF electrodes at other positions, which provide at least partial overlap of the RF electric field and the ultrasound radiation within the adipose tissue. FIG. 11 shows schematically another possible arrangement of the RF electrodes and the ultrasound transducers in side view (FIG. 11a), and in top view (FIG. 11b). For simplicity, FIG. 11 shows only one pair of RF electrodes 91 and 92, and a pair of ultrasound transducers 93 and 94.

Preferred RF parameters, for all the embodiments, are: RF frequency between 100 kHz and 50 MHz, more preferred between 500 kHz and 5 MHz. Applied RF voltages are between 10V peak to 1000V peak, more preferred between 30V peak to 300V peak for a distance of 10 mm between electrodes, and higher voltage for greater electrode spacing. The RF electrode spacing may be between 5 mm to 50 mm and their length may be between 5 mm to 50 mm. Preferably, the ultrasound transducer covers most of the area between the electrodes. The ultrasound transducer may be flat with uniform phase where the depth of treatment is controlled by the frequency, or a fixed focus transducer or a phased array transducer with the capability of scanning the focal volume, as in embodiments 3a-3d. Preferably, the RF energy is applied in pulses, typically between 10 μsec 500 msec, more preferred between 1 msec to 100 msec. Preferably the RF and ultrasound pulses overlap at least partially.

Monitoring the contact between the RF electrodes and the body may be done by measuring the voltage across the electrodes and the current, and calculating from that the impedance between the electrodes. Based on experience with a certain electrode structure, a range of impedances can be defined that are sufficient for the application of the RF power. As in the previous embodiments, coupling of the ultrasound energy to the body can be monitored by measuring the transducer impedance.

The applicator embodiments 3b-3g are independent of any specific physical model for the destruction of fat cells. However, it is advantageous in all embodiments to apply the ultrasound energy in a way that maximizes the selective destruction of fat cells, as was done with embodiment 3a, namely, to exploit the unique structure of fat cells to effect relative movement between the adipose cell constituents, leading to strain and selective heating at the cell boundary, following by damage to the cell membrane which cause cell necrosis or apoptosis.

Any of the above embodiments may be adapted for delivering infra-red (IR) energy to the skin surface. Delivering of IR illumination to the skin enhances the aesthetic treatment, so that fat, cellulites and skin can be treated simultaneously. The IR illumination can be applied to skin regions not covered by the ultrasound transducer or the RF electrodes.

The invention claimed is:

1. An applicator for selective treatment of adipose tissue, the applicator comprising:
   a hollow dome comprising an interior chamber communicating through a port with a vacuum pump, the hollow dome configured to be applied to a skin to suction the skin and a subcutaneous tissue into the interior chamber, forming a protrusion protruding above a surrounding surface of the skin, the protrusion including an adipose tissue;
   one or more moderately focused ultrasound transducers located in the interior chamber of the hollow dome generating ultrasound energy with focal volumes located in the protrusion of the adipose tissue, and generating a power flow density of the ultrasound energy lower than the threshold for cavitation in the adipose tissue being treated, however sufficient to generate pressure gradients in the focal volumes;
   a pair of radio frequency (RF) electrodes located at sides of the hollow dome and electrically isolated from the hollow dome and the one or more moderately focused ultrasound transducers, the RF electrodes driven by an RF driver operative to provide RF energy to the RF electrodes such that when both the RF electrodes are in contact with the skin the RF energy creates a high electric field in the adipose tissue, wherein the RF electrodes comprising a thin film of electrically conducting material having negligible ultrasound attenuation applied to each face of the one or more moderately focused ultrasound transducers when both the RF electrodes touch the skin; and
   a cavitation sensor comprising a receiver tuned to half the moderately focused ultrasound transmitting frequency, the receiver configured to detect and control an appearance of cavitation in the tissue being treated and control a pressure level such that the pressure level does not cause cavitation in lipid, cytoplasm, and intercellular fluids of the tissue being treated.

2. The applicator according to claim 1, wherein regions of maximum electric field and ultrasound focal volumes at least partially overlap within the adipose tissue, to maximize a combined effects of simultaneously applied the RF energy and the ultrasound energy.

3. The applicator according to claim 1, wherein the one or more moderately focused ultrasound transducers emit ultrasound that heats the adipose tissue in the focal volumes and increases the RF conductivity such that more energy is delivered by the RF energy into the same heated focal volumes yielding a combined stress and reducing a cell strength of the adipose tissue.

4. The applicator according to claim 3, wherein a temperature of the heated focal volumes is kept below 44 degrees Celsius.

5. The applicator according to claim 1, wherein the electric field created in the adipose tissue heats minority fluids in the adipose tissue and generates additional strain on cell membranes of the adipose tissue.

6. The applicator according to claim 1, wherein the one or more moderately focused ultrasound transducers are one of a group of transducers consisting of flat transducers, curved transducers or transducers with a lens.

7. The applicator according to claim 6, wherein the one or more moderately focused ultrasound transducers are phased array transducers and wherein phases of the array transducers are controlled, and matched in a way that maximizes the ultrasound intensity in the focal volumes and the pressure gradients in the focal volumes.

8. The applicator according to claim 1, wherein the one or more moderately focused ultrasound transducers in the interior chamber are oriented so that the direction of ultrasound radiation from the transducers is parallel to surface of the skin outside the protrusion in order to avoid penetration of ultrasound energy to internal tissues and organs below the adipose tissue.

9. The applicator according to claim 1, wherein the one or more moderately focused transducers provide moderately focused ultrasound energy confined to a view angle of less than 120 degrees for selective treatment of adipose tissue.

10. The applicator according to claim 1, wherein the one or more moderately focused transducer provide moderately focused ultrasound energy confined to a view angle of less than 90 degrees for selective treatment of adipose tissue.

11. The applicator according to claim 1, wherein the one or more moderately focused ultrasound transducers generate a pressure gradient between 2 GPa/m to 15 GPa/im and the ultrasound energy has a frequency lower than 1 MHz.

12. The applicator according to claim 1, wherein the ultrasound energy is monitored by measuring an electrical impedance of the one or more moderately focused ultrasound transducer, and variations in power transmission from the one or more moderately focused ultrasound transducer are manifested by changes in a voltage-current relation on the one or more moderately focused ultrasound transducer.

13. The applicator according to claim 1, wherein the pressure gradients generate a relative movement between fat cell constituents having different densities.

14. The applicator according to claim 1, wherein the RF electrodes, are one of a group of electrodes consisting of conductive electrodes for direct injection of current to the skin, and electrodes insulated by a thin layer of insulating material for capacitive coupling of energy to the adipose tissue.

15. The applicator according to claim 1, further comprising a processor for monitoring a contact between the RF electrodes and the skin is done by measuring a voltage across the RF electrodes and a current, and calculating from the voltage and the current an impedance between the RF electrodes, and monitoring a coupling of the one or more moderately focused ultrasound transducers to the skin by measuring a transducer impedance.

16. The applicator according to claim 1, wherein the one or more moderately focused ultrasound transducers enhance pressure gradient at an expense of pressure amplitude at the focal volumes and obtain selective treatment of the adipose tissue without cavitation.

17. The applicator according to claim 1, wherein the power flow density is at 700 W/cm2 or below.

18. An applicator for selective treatment of adipose tissue, the applicator comprising:
   a hollow dome comprising an interior chamber communicating through a port with a vacuum pump, the hollow dome configured to be applied to a skin to suction the skin and a subcutaneous tissue into the interior chamber, forming a protrusion protruding above a surrounding surface of the skin, the protrusion including an adipose tissue;
   one or more moderately focused ultrasound transducers located in the interior chamber of the hollow dome and generating ultrasound energy with focal volumes located in the protrusion of the adipose tissue, the one or more moderately focused ultrasound transducers, generating a power flow density of the ultrasound energy lower than a threshold for cavitation, however, sufficient to, generate pressure, gradients in the focal volumes in the adipose tissue being treated;
   a pair of radio frequency (RF) electrodes located at sides of the hollow dome and electrically isolated from the hollow dome and the one or more moderately focused ultrasound transducers, the RF electrodes driven by an RF driver operative to provide RF energy to the RF electrodes such that when both the RF electrodes are in contact with the skin the RF energy creates a high electric field in the adipose tissue, the RF electrodes comprising a thin film of electrically conducting material having negligible ultrasound attenuation applied to each face of the one or more moderately focused ultrasound transducers when both the RF electrodes touch the skin, and
   a cavitation sensor comprising a receiver tuned to half the moderately focused ultrasound transmitting frequency, the receiver configured to detect and control an appearance of cavitation in the tissue being treated and control a pressure level such that the pressure level does not cause cavitation in lipid, cytoplasm and intercellular fluids of the tissue being treated.

* * * * *